(12) United States Patent
Wollenweber et al.

(45) Date of Patent: Jul. 6, 2004
(10) Patent No.: US 6,759,371 B2

(54) BROMOXYNIL COMPONENT-CONTAINING HERBICIDAL PREPARATIONS WITH ENHANCED PENETRATION AND METHODS OF USING SAME

(75) Inventors: Horst-Werner Wollenweber, Duesseldorf (DE); Hans-Georg Mainx, Leichlingen (DE); Benoit Abribat, Dannemois (FR); Hans De Ruiter, Wageningen (NL)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 10/169,521

(22) PCT Filed: Dec. 23, 2000

(86) PCT No.: PCT/EP00/13266
§ 371 (c)(1),
(2), (4) Date: Dec. 2, 2002

(87) PCT Pub. No.: WO01/50861
PCT Pub. Date: Jul. 19, 2001

(65) Prior Publication Data
US 2003/0125210 A1 Jul. 3, 2003

(30) Foreign Application Priority Data
Jan. 7, 2000 (DE) .......................................... 100 00 320

(51) Int. Cl.[7] .............................................. A01N 37/34
(52) U.S. Cl. ..................................................... 504/310
(58) Field of Search ......................................... 504/310

(56) References Cited

U.S. PATENT DOCUMENTS

| | | | |
|---|---|---|---|
| 4,813,999 A | 3/1989 | Schapira et al. | ............... 71/105 |
| 5,021,083 A | * 6/1991 | Schapira et al. | ............... 71/105 |

FOREIGN PATENT DOCUMENTS

| | | |
|---|---|---|
| DE | 29 24 403 A1 | 12/1980 |
| DE | 268 147 A1 | 5/1989 |
| DE | 199 08 559 A1 | 9/2000 |
| EP | 0 485 207 B1 | 5/1992 |
| GB | 1050497 | 5/1965 |
| GB | 2 190 589 A | 11/1987 |
| WO | WO 90/13533 A1 | 11/1990 |
| WO | WO 91/15441 A1 | 10/1991 |
| WO | WO 00/51427 A1 | 9/2000 |

OTHER PUBLICATIONS

Römpp, Lexikon Chemie, 10th Edition, (1997), p. 1764.

* cited by examiner

*Primary Examiner*—S. Mark Clardy
(74) *Attorney, Agent, or Firm*—Aaron R. Ettelman

(57) ABSTRACT

Herbicidal preparations which contain: (a) water; (b) a bromoxynil component; and (c) at least one compound corresponding to the general formula (I):

$$RO-(C_2H_4O)_n(C_3H_6O)_m-R' \qquad (I)$$

wherein RO represents an alcohol moiety selected from the group consisting of $C_{1-6}$ monohydric alcohols, and $C_{2-12}$ polyols having from 2 to 6 hydroxyl groups; n represents a number of from 1 to 50; m represents a number of from 0 to 10; and wherein each R' represents a substituent independently selected from the group consisting of hydrogen and an ester group of the general formula, —CO—R", wherein each R" independently represents an alkyl group having from 5 to 29 carbon atoms; with the proviso that at least one R' represents —CO—R", are described. Also described is the enhanced penetration of leaves by bromoxynil-containing herbicidal preparations via the addition of at least one compound corresponding to the general formula (I), as well as methods for controlling plant growth using such preparations.

20 Claims, No Drawings

BROMOXYNIL COMPONENT-CONTAINING HERBICIDAL PREPARATIONS WITH ENHANCED PENETRATION AND METHODS OF USING SAME

BACKGROUND OF THE INVENTION

This invention relates to water-based herbicidal preparations containing at least one agrochemical agent from the group consisting of bromoxynil and its derivatives and certain alkoxylated fatty acid esters, to the use of such fatty acid esters for increasing the penetration of bromoxynil and its derivatives into plant leaves and to a process for controlling unwanted plant growth.

It is known that weeds can be controlled with a variety of herbicides which often have little or no solubility in water. One important representative is bromoxynil (3,5-dibromo-4-hydroxybenzonitrile) and its derivatives. Where herbicidal agents such as these are applied, penetration into the plant is minimal on account of their poor solubility in water, resulting in an inadequate herbicidal effect. Accordingly, agrochemical agents of the type in question are formulated as aqueous dispersions or emulsions so that they can be applied without difficulty, for example by spraying onto the plants, the emulsifier also acting as a wetting agent to improve uptake of the agent into the plant. The greater the penetration of the herbicide, the more effectively and efficiently it can be used. Accordingly, there is a general need for formulations which provide for substantially complete penetration of the herbicidal agent into the plant. DE-OS 29 24 403, for example, describes water-based preparations containing bromoxynil salts and—as formulation aids—alkali metal salts of alkyl polyglycol ether phosphate partial esters. EP 0 485 207 describes aqueous emulsions containing bromoxynil octanoate and heptanoate and, as emulsifiers, polyalkylene oxide-modified silanes or ethoxylated tall oil amides.

It has surprisingly been found that water-based preparations containing bromoxynil or derivatives thereof and, as emulsifiers, certain alkoxylated alcohols provide for very high penetration of the herbicide into the plant.

BRIEF SUMMARY OF THE INVENTION

This invention relates to water-based herbicidal preparations containing at least one agrochemical agent from the group consisting of bromoxynil and its derivatives and certain alkoxylated fatty acid esters, to the use of such fatty acid esters for increasing the penetration of bromoxynil and its derivatives into plant leaves and to a process for controlling unwanted plant growth.

Accordingly, the present invention relates to water-based preparations containing bromoxynil or derivatives thereof and one or more compounds corresponding to general formula (I):

$$RO-(C_2H_4O)_n(C_3H_6O)_m-R' \quad (I)$$

in which RO is an alcohol selected from the group of branched or linear, saturated or unsaturated monohydric alcohols containing 1 to 6 carbon atoms or polyols containing 2 to 12 carbon atoms and 2 to 6 hydroxyl groups and R' is hydrogen and/or a group —CO—R", where R" is a branched or linear, saturated or unsaturated alkyl group containing 5 to 29 carbon atoms, n is a number of 1 to 50 and m is 0 or a number of 1 to 10.

DETAILED DESCRIPTION OF THE INVENTION

The preparations according to the invention contain bromoxynil and/or derivatives thereof, preferably bromoxynil alkyl esters or sodium and/or potassium salts of bromoxynil or sulfates and carbonates thereof. Preparations containing bromoxynil octanoate or heptanoate are particularly preferred.

The alkoxylated compounds corresponding to formula (I) are known substances which are described, for example, in U.S. Pat. Nos. 2,678,935, 3,539,518, 4,022,808 or GB 1,050,497 of which the disclosures are also part of the present invention.

The compounds corresponding to formula (I) may by prepared by any methods known to the expert, for example by esterification of fatty acids with alkoxylated methanol, as described in U.S. Pat. No. 3,539,518. Unfortunately, this process has certain disadvantages. It is a two-stage process, the esterification reaction is very time-consuming and the products are colored by the high reaction temperatures. In addition, fatty acid methylester ethoxylates produced by this process have relatively high OH values after the esterification step which can be problematical for certain applications. Another possibility is the direct reaction of fatty acid esters with alkylene oxides in the presence of transition metal catalysts, as described in U.S. Pat. No. 4,022,808. However, the fatty acid alkyl ester alkoxylates are preferably produced by the heterogeneously catalyzed direct alkoxylation of fatty acid alkyl esters with ethylene oxide and/or propylene oxide on calcined or hydrophobicized hydrotalcites. These synthesis processes are described in detail in WO 90/13533 and WO 91/15441 of which the disclosure is also part of the present invention. The products formed are distinguished by a low OH value, the reaction is carried out in a single stage and light-colored products are obtained. The fatty acid alkyl esters used as starting materials may be obtained from natural oils and fats or may be synthetically produced.

The alkoxylated fatty acid esters contain at least 1 mol ethylene oxide groups per mol ester. Compounds of formula (I) containing between 1 and 30 mol ethylene oxide per mol ester are preferred. In addition to the ethylene oxide units, between 1 and 10 propylene oxide groups are also present in the molecule. Other preferred compounds corresponding to formula (I) are those which contain between 1 and 30 mol ethylene oxide per mol ester and 1 to 10 mol propylene oxide groups. For these mixed ethylene oxide/propylene oxide adducts, it is possible to use both compounds reacted with a mixture of ethylene oxide and propylene oxide and compounds reacted with ethylene oxide and propylene oxide in two separate steps. The alkoxides are statistically distributed between the OH groups present, depending on the production process.

If compounds corresponding to formula (I) containing polyols as the alcohol component RO are used, the quantitative data for the ethylene or propylene oxide units (indices n and m) are always based on the molecule as a whole. However, the exact distribution of the ethylene or propylene oxide units between the various hydroxyl groups of the polyols is known to comply with a distribution dependent on the synthesis process.

The fatty acid esters —CO—R" contain alkyl groups R" with 5 to 29 carbon atoms. Suitable fatty acid components are natural or synthetic fatty acids, more particularly straight-chain, saturated or unsaturated $C_{6-30}$ fatty acids, including technical mixtures thereof obtainable by lipolysis from animal and vegetable fats and oils, for example from coconut oil, palm kernel oil, soybean oil, sunflower oil, rapeseed oil, cottonseed oil, fish oil, bovine tallow and lard; special examples are caprylic, capric, lauric, lauroleic, myristic, myristoleic, palmitic, palmitoleic, oleic, elaidic, arachic, gadoleic, behenic and erucic acid.

Suitable alcohol components RO are linear or branched, saturated or unsaturated monohydric alcohols containing 1 to 6 carbon atoms, for example methanol, ethanol, n- and i-propanol, n- and i-butanol, pentanol, hexanol, 2-ethylhexanol and cyclohexanol. Suitable $C_{2-6}$ polyols are, for example, ethylene glycol, 1,2-propylene glycol, 1,2-butylene glycol, glycerol or trimethylol propane and pentaerythritol.

Basically, all the hydroxyl groups of the alcohols are substituted by the alkoxides although not all terminal alkoxide groups are capped by ester groups. Accordingly, if polyols, such as glycerol or ethylene glycol, are used as the alcohol component RO, the preparations may contain compounds corresponding to formula (I) obtained by reaction both of the full esters and of the partial esters with alkoxides. However, preferred compounds of formula (I) are those in which all the hydroxyl groups of the alcohols are alkoxylated and all terminal alkoxide groups are capped by ester groups with the formula —CO—R". Accordingly, in these preferred compounds, R" in formula (I) stands exclusively for a branched or linear, saturated or unsaturated alkyl group containing 5 to 29 carbon atoms.

In addition, alkoxylated fatty acid esters corresponding to formula (I) of which the fatty acid component is selected from linear, unbranched $C_{6-18}$ fatty acids and of which the alcohol component is methanol, the esters (I) preferably containing between 1 and 3 mol propylene oxide and between 1 and 6 mol ethylene oxide per mol ester, are preferably used in the preparations according to the invention. Compounds such as these can be obtained, for example, by the above-described reactions of palmitic, stearic, oleic, linoleic or linolenic acid, lauric acid and myristic acid or esters thereof with alkoxides.

Also suitable are alkoxylated compounds where the alcohol component is glycerol and the fatty acid component is selected from saturated or unsaturated, branched or unbranched fatty acids containing 18 to 22 carbon atoms and the esters contain between 1 and 3 mol ethylene oxide per mol ester. Compounds of formula (I) in which n is 5, 10 or 30 and m is 0 are particularly preferred. Compounds such as these can be obtained, for example, by reacting glycerol esters of natural fatty acids, such as, for example, palm oil, rapeseed oil, soybean oil or preferably castor oil, with ethylene oxide.

The compounds of formula (I) present in the preparations according to the invention are nonionic compounds which may also be characterized by their HLB value (hydrophilic/lipophilic balance according to Griffin's definition; see R ömpp, Lexikon Chemie, 10th Edition 1997, page 1764). Preferred preparations contain compounds of formula (I) with HLB values of 4 to 10 and preferably 5 to 9.

The preparations contain at least bromoxynil or derivatives thereof as herbicides although mixtures with various other herbicides may also be used. The preparations according to the invention may contain the herbicide in enriched form, in which case they are formulated as concentrates containing more than 50% by weight to at most 90% by weight of herbicidal agent. However, they may also be present in dilute form. Preferred preparations contain between 0.01 and 5% by weight of bromoxynil or derivatives thereof, based on the weight of the preparation. If the preparations contain other agrochemical agents, they are present in quantities of 0.01 to 10% by weight. The percentage water content of the preparations according to the invention is preferably between 10 and 99.9% by weight. The quantity ratio between the compounds of formula (I) and the herbicidal agents is preferably between 1:1 and 1:100. Particularly preferred preparations are those in which the ratio by weight between the compounds of formula (I) and the herbicidal agents is in the range from 1:10 to 1:80 and more particularly in the range from 1:2 to 1:5.

Besides bromoxynil and its derivatives and the compounds of formula (I), the water-based preparations according to the invention may contain other typical ingredients and additives. These include solvents, such as ethylene or propylene glycols and $C_{1-6}$ alcohols, solid carriers, such as lignin, lignin derivatives or clays and other known emulsifiers or dispersants. However, preparations containing only emulsifiers corresponding to formula (I) and no other emulsifiers or dispersants are particularly preferred. Most particularly preferred preparations are those which are free from colloids, such as titanium dioxide, and/or free from solvents, more particularly mineral-oil-based solvents.

The preparations according to the invention are stable in storage, even at temperatures above 30° C., and can be produced without intensive shearing, for example by manual stirring. The preparations according to the invention are formed without intensive shearing, for example by simple manual stirring. To this end, the compounds of formula (I) may be initially introduced into a mixing vessel, for example in liquid form. The herbicidal agent is then added and the resulting mixture is dispersed in water. If compounds of formula (I) with melting points above room temperature are used, they may be used in molten form. However, compounds corresponding to formula (I) with a melting point below 25° C. are preferably used. Alternatively, a mixture of the agrochemical agent in water may also be prepared in a first step and the mixture thus prepared may be subsequently emulsified or dispersed by addition of compounds corresponding to formula (I).

The present invention also relates to a process for controlling unwanted plants in which a water-based bromoxynil-containing preparation as described in the foregoing is applied to the leaves of the plants by any method known to the expert in such quantities that the plants die off.

The present invention also relates to the use of compounds corresponding to formula (I) for increasing the penetration of bromoxynil or its derivatives into plant leaves.

EXAMPLES

Six aqueous bromoxynil Na salt emulsions were prepared. They were either free from emulsifiers or contained known emulsifiers and were compared with a preparation according to the invention containing as additive a compound corresponding to formula (I) in which RO=glycerol, R'=COR" with R"=$C_{16-18}$, m=0, n=30.

The emulsifiers were present in quantities of 0.5% by weight, based on the preparation as a whole. The concentration of the sodium salt of the bromoxynil was 4.1 mM. Quantities of 0.1 μl of the water-based preparations were applied to the first leaves of deadly nightshade. Penetration into the leaves was measured after 24 hours. The results are set out in Table 2.

TABLE 1

| Test | Emulsifier |
|------|------------|
| (1)  | —          |
| (2)  | C$_{8-10}$ Alkyl (oligo)glucoside |
| (3)  | C$_{6-10}$ Fatty acid methyl ester + 3 EO |
| (4)  | C$_{6-10}$ Fatty acid methyl ester + 6 EO |
| (5)  | Nonylphenol + 10 EO |
| (6)  | Triglyceride according to the invention |

TABLE 2

| Test | Penetration after 24 h in % |
|------|------------------------------|
| (1)  | 0  |
| (2)  | 2  |
| (3)  | 22 |
| (4)  | 56 |
| (5)  | 42 |
| (6)  | 82 |

The results show the increase in the penetration of bromoxynil achieved by adding the preparations according to the invention.

What is claimed is:

1. A herbicidal preparation comprising: (a) water; (b) a bromoxynil component; and (c) at least one compound corresponding to general formula (I):

RO—(C$_2$H$_4$O)$_n$(C$_3$H$_6$O)$_m$—R'  (I)

wherein RO represents an alcohol moiety selected from the group consisting of C$_{1-6}$ monohydric alcohols, and C$_{2-12}$ polyols having from 2 to 6 hydroxyl groups; n represents a number of from 1 to 50; m represents a number of from 0 to 10; and wherein each R' represents a substituent independently selected from the group consisting of hydrogen and an ester group of the general formula, —CO—R", wherein each R" independently represents an alkyl group having from 5 to 29 carbon atoms; with the proviso that at least one R" represents —CO—R".

2. The preparation according to claim 1, wherein the bromoxynil component comprises a derivative selected from the group consisting of bromoxynil alkyl esters, bromoxynil sulfates and salts thereof, bromoxynil carbonates and salts thereof, and mixtures thereof.

3. The preparation according to claim 1, wherein the bromoxynil component comprises an alkyl ester selected from the group consisting of bromoxynil octanoate and bromoxynil heptanoate.

4. The Preliminary according to claim 1, wherein the bromoxynil component comprises a salt selected from the group consisting of sodium and potassium salts of bromoxynil.

5. The preparation according to claim 1, wherein the bromoxynil component is present in an amount of from 0.01 to 5% by weight, based on the preparation.

6. The preparation according to claim 2, wherein the bromoxynil component is present in an amount of from 0.01 to 5% by weight, based on the preparation.

7. The preparation according to claim 1, wherein each R' represents an ester group of the general formula, —CO—R".

8. The preparation according to claim 7, wherein each R' represents an ester group of the general formula, —CO—R".

9. The preparation according claim 1, wherein RO represents a glycerol moiety and R" represents an alkyl group having from 17 to 21 carbon atoms.

10. The preparation according to claim 7, wherein RO represents a glycerol moiety and each R" represents an alkyl group having from 17 to 21 carbon atoms.

11. The preparation according to claim 1, wherein n represents a number of from 1 to 30 and m represents a number of from 0 to 5.

12. The preparation according to claim 1, wherein n represents a number selected from the group consisting of 5, 10 and 30 and m represents 0.

13. The preparation according to claim 1, wherein RO represents a glycerol moiety and —CO—R" represents a ricinoleic acid moiety.

14. The preparation according to claim 7, wherein RO represents a glycerol moiety and each —CO—R" represents a ricinoleic acid moiety.

15. The preparation according to claim 1, wherein RO represents a methanol moiety and R" represents an alkyl group having from 5 to 17 carbon atoms.

16. The preparation according to claim 1, wherein the at least one compound corresponding to the general formula (I) has an HLB value of from 4 to 10.

17. The preparation according to claim 1, wherein the bromoxynil component comprises a derivative selected from the group consisting of bromoxynil alkyl esters, bromoxynil sulfates and salts thereof, bromoxynil carbonates and salts thereof, and mixtures thereof, and wherein the at least one compound corresponding to the general formula (I) has an HLB value of from 4 to 10.

18. A herbicidal preparation comprising: (a) water; (b) a bromoxynil component selected from the group consisting of bromoxynil alkyl esters, bromoxynil sulfates and salts thereof, bromoxynil carbonates and salts thereof, and mixtures thereof, present in an amount of from 0.01 to 5% by weight, based on the preparation; and (c) at least one compound corresponding to the general formula (I):

RO—(C$_2$H$_4$O)$_n$(C$_3$H$_6$O)$_m$—R'  (I)

wherein RO represents a glycerol moiety; n represents a number of from 5 to 30; m represents 0; and wherein each R' represents an ester group of the general formula, —CO—R",wherein each R" represents an alkyl group having from 16 to 18 carbon atoms.

19. A method of enhancing penetration of bromoxynil-containing herbicidal preparations into plant leaves, said method comprising:
 (a) providing an aqueous, bromoxynil component-containing herbicidal preparation;
 (b) combining the preparation with at least one compound corresponding to the general formula (I), to form an enhanced preparation:

RO—(C$_2$H$_4$O)$_n$(C$_3$H$_6$O)$_m$—R'  (I)

wherein RO represents an alcohol moiety selected from the group consisting of C$_{1-6}$ monohydric alcohols, and C$_{2-12}$ polyols having from 2 to 6 hydroxyl groups; n represents a number of from 1 to 50; m represents a number of from 0 to 10; and wherein each R' represents a substituent independently selected from the group consisting of hydrogen and an ester group of the general formula, —CO—R", wherein each R" independently represents an alkyl group having from 5 to 29 carbon atoms; with the proviso that at least one R' represents —CO—R"; and
 (c) contacting a plant substrate with the enhanced preparation.

20. A method of controlling plant growth, said method comprising:
 providing a preparation according to claim 1; and contacting an unwanted plant with said preparation, such that said unwanted plant dies.

* * * * *